(12) United States Patent
Sadeghian Marnani

(10) Patent No.: US 9,329,202 B2
(45) Date of Patent: May 3, 2016

(54) CALIBRATION OF A MECHANICAL PROPERTY OF SPM CANTILEVERS

(71) Applicant: Nederlandse Organisatie voor toegepast-natuurwetenschappelijk onderzoek TNO, Delft (NL)

(72) Inventor: Hamed Sadeghian Marnani, Delft (NL)

(73) Assignee: NEDERLANDSE ORGANISATIE VOOR TOEGEPAST-NATUUR-WETENSCHAPPELIJK ONDERZOEK TNO, Delft (NL)

( * ) Notice: Subject to any disclaimer, the term of this patent is extended or adjusted under 35 U.S.C. 154(b) by 42 days.

(21) Appl. No.: 14/389,933

(22) PCT Filed: Mar. 22, 2013

(86) PCT No.: PCT/NL2013/050210
§ 371 (c)(1),
(2) Date: Oct. 1, 2014

(87) PCT Pub. No.: WO2013/151425
PCT Pub. Date: Oct. 10, 2013

(65) Prior Publication Data
US 2015/0293145 A1 Oct. 15, 2015

(30) Foreign Application Priority Data
Apr. 2, 2012 (EP) .................................. 12162847

(51) Int. Cl.
*G01Q 40/00* (2010.01)
*B81C 99/00* (2010.01)
(Continued)

(52) U.S. Cl.
CPC ............. *G01Q 40/00* (2013.01); *B81C 99/003* (2013.01); *B82Y 35/00* (2013.01); *G01N 29/036* (2013.01); *G01N 29/30* (2013.01); *G01N 2291/0427* (2013.01)

(58) Field of Classification Search
None
See application file for complete search history.

(56) References Cited

U.S. PATENT DOCUMENTS 5,719,324 A * 2/1998 Thundat ............... G01N 29/022
422/88
6,016,686 A * 1/2000 Thundat ................ B81B 3/0021
422/83

(Continued)

FOREIGN PATENT DOCUMENTS

JP        11-094859        4/1999
WO      2005/098869 A1   10/2005

OTHER PUBLICATIONS

Shen, Sheng et al., "Thermal conductance of bimaterial microcantilevers", Applied Physics Letters, AIP, American Institute of Physics, vol. 92, No. 6, pp. 63509-63509, Feb. 13, 2008.

(Continued)

*Primary Examiner* — Michael Logie
(74) *Attorney, Agent, or Firm* — Knobbe, Martens, Olson & Bear, LLP

(57) ABSTRACT

A method is presented for calibrating a cantilever, such as a scanning probe microscope cantilever (SPM cantilever). The cantilever to be calibrated comprises at least a first and a second layer having a mutually different thermal expansion coefficient, the method comprising the steps of: controllably causing a temperature distribution along the cantilever, measuring a spatial state of the cantilever, computing a mechanical property from the observed spatial state caused by controllably changing the temperature. Also a calibration arrangement and a scanning probe microscope provided with the calibration arrangement are presented.

11 Claims, 8 Drawing Sheets

(51) Int. Cl.
  *B82Y 35/00* (2011.01)
  *G01N 29/036* (2006.01)
  *G01N 29/30* (2006.01)

(56) References Cited

U.S. PATENT DOCUMENTS

| | | | | |
|---|---|---|---|---|
| 6,050,722 | A * | 4/2000 | Thundat | G01J 5/20 374/121 |
| 6,096,559 | A * | 8/2000 | Thundat | G01N 29/036 422/51 |
| 6,118,124 | A * | 9/2000 | Thundat | G01J 1/04 250/332 |
| 6,312,959 | B1 * | 11/2001 | Datskos | B81B 3/0018 436/147 |
| 8,914,910 | B1 * | 12/2014 | Sadeghian Marnani | G01Q 40/00 850/19 |
| 2002/0092340 | A1 * | 7/2002 | Prater | G02B 7/1821 73/24.02 |
| 2003/0137216 | A1 * | 7/2003 | Tamayo de Miguel | B82Y 35/00 310/311 |
| 2008/0011065 | A1 * | 1/2008 | Su | B82Y 35/00 73/105 |
| 2013/0047303 | A1 * | 2/2013 | King | B82Y 35/00 850/56 |
| 2013/0276175 | A1 * | 10/2013 | King | B82Y 35/00 850/40 |

OTHER PUBLICATIONS

Cook, S.M. et al., "Practical implementation of dynamic methods for measuring atomic force microscope cantilever spring constants", Nanotechnology, vol. 17, No. 9, pp. 2135-2145, May 14, 2006.
International Search Report dated May 10, 2013 for PCT/NL2013/050210.

* cited by examiner

CALIBRATION OF A MECHANICAL PROPERTY OF SPM CANTILEVERS

BACKGROUND OF THE INVENTION

1. Field of the Invention

The present invention relates to an arrangement for calibrating a mechanical property of cantilevers, such as cantilevers for scanning probe microscopes and micro indentation devices.

The present invention further relates to a scanning probe microscope including such an arrangement.

The present invention further relates to a method for calibrating a mechanical property of such cantilevers.

2. Related Art

Scanning probe microscopes (SPM), such as atomic force microscopes s are widely used for the physical characterization of materials and devices when high spatial resolution and small feature sizes are of interest. SPMs are primarily used in imaging modes to provide topographic information, but they can also record the force interaction between a sensor tip of the cantilever and a sample.

Measuring the force interaction between the tip and surface involves measuring the deflection of a spring suspension. In the case of an SPM, the force sensor itself usually is a micro-fabricated cantilever that functions as a passive mechanical sensor. The micro-fabricated cantilever typically comprises a substrate layer, such as a silicon layer or a silicon nitride layer that is provided with a cover layer having a high reflectance, such as gold or aluminum. The deflection of the cantilever is typically determined by measuring the position to which a laser beam impingent on this cover layer is reflected. A force acting on the cantilever can then be calculated provided that a spring constant of the cantilever is known. However, process non-uniformities and variations during fabrication of the cantilever, contaminations and imperfections lead to uncertainties in cantilever's spring constant. Therefore, a calibration of the cantilevers is essential to enable reliable measurements. Similar probes are used in other instruments, such as indentation machines.

It is noted that SHEN SHENG ET AL disclose in: "Thermal conductance of biomaterial microcantilevers", APPLIED PHYSICS LETTERS, MP, AMERICAN INSTITUTE OF PHYSICS, MELVILLE, N.Y., US, vol. 92, no. 6, 13 Feb. 2008, pages 63509-63509, D1 how the effective thermal conductance of a cantilever and the temperature at the tip of the cantilever can be determined by measuring the bending of the cantilever in response to two different thermal inputs: power absorbed at the tip and ambient temperature.

Furthermore it is noted that COOK S M ET AL compare two measurement methods in: "Practical implementation of dynamic methods for measuring atomic force microscope cantilever spring constants", NANOTECHNOLOGY, IOP, BRISTOL, GB, vol. 17, no. 9, 14 May 2006, pages 2135-2145. The two measurement methods of atomic force microscope cantilever spring constants (k) compared therein are the thermal noise and Sader methods. Cook et al. select these methods for comparison as they are considered commonly applicable and relatively user-friendly, providing an in situ, non-destructive, fast measurement of k for a cantilever independent of its material or coating.

According to the thermal noise method the spring constant is calculated from the temperature T of the cantilever and the corresponding thermal vibration spectrum

SUMMARY OF THE INVENTION

According to embodiments of the present invention a temperature distribution along the cantilever is controllably provided and the effect thereof on a spatial state of the cantilever is determined. Knowing the temperature distribution and the spatial state of the cantilever the spring constant of the cantilever can be extracted, for calibration thereof.

The spatial state of the cantilever is considered to include a deflection of the cantilever, a curvature of the cantilever or a derivative of thereof, and the eigenfrequency (resonance frequency) with which the cantilever oscillates if it is excited.

Contrary to the method of Shen Sheng et al. mentioned above, both the deflection (or curvature) and the resonance frequency are measured and used for determining the spring constant of the cantilever. This is particularly advantageous in that the Young modulus of the layers of the cantilever need not be known. It is noted that Cook et al mention a measurement of a frequency spectrum. However, the method disclosed by Cooke et al does not specifically use the resonance frequency for computation of the mechanical property. In particular Cooke et al. do not disclose that the measured resonance frequency is used as well as the measured deflection or radius of curvature for computation of the mechanical property. It is considered a disadvantage that the latter method is not suitable for calibration of stiff cantilevers, i.e. having a stiffness above 40 N/m. Moreover it is a disadvantage of this known method that the position of the laser spot on the cantilever and its size can influence the result of a thermal noise measurement.

More in particular, according to a first aspect of the invention an arrangement for calibrating a cantilever is provided as claimed in claim 1.

According to a second aspect of the invention a scanning probe microscope is provided as claimed in claim 6.

According to a third aspect of the invention a method for calibrating a cantilever is provided as claimed in claim 7.

Controllably applying a temperature distribution along the cantilever can be achieved in various ways, for example by irradiating the cantilever to be calibrated by a photon radiation source, such as a laser. Alternatively, a temperature distribution along the cantilever may be controllably applied by modifying the temperature of the environment. The latter embodiment is particularly suitable for massive parallel calibration, as it is not necessary to manipulate the cantilevers individually. The temperature of the environment is mainly determined by a temperature of a location where the cantilever is clamped, as at that location the strongest heat exchange with the environment takes place. However, heat exchange with the environment may also take place in other ways, such as by radiation, and if the cantilever to be calibrated is arranged in a medium, also by conduction through the medium as well as by convection of the medium, dependent on the type of medium and the pressure thereof.

BRIEF DESCRIPTION OF THE DRAWINGS

These and other aspects are described in more detail with reference to the drawing. Therein.

DETAILED DESCRIPTION OF EMBODIMENTS

Figure 1:
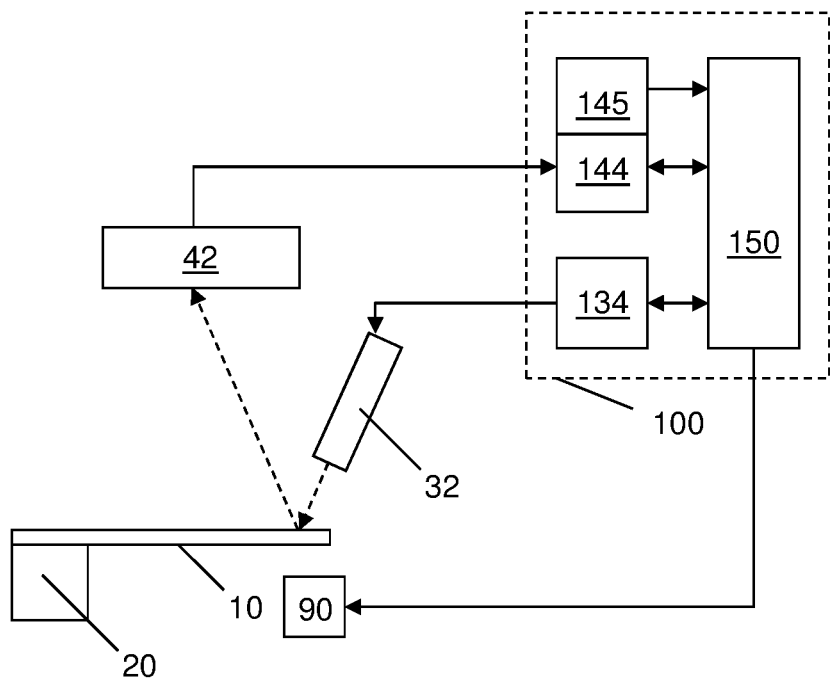
FIG. 1 shows a first embodiment of an arrangement according to the first aspect of the invention.

Like reference symbols in the various drawings indicate like elements unless otherwise indicated.

In the following detailed description numerous specific details are set forth in order to provide a thorough understanding of the present invention. However, it will be understood by one skilled in the art that the present invention may be practiced without these specific details. In other instances, well known methods, procedures, and components have not been described in detail so as not to obscure aspects of the present invention.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Figure 2:
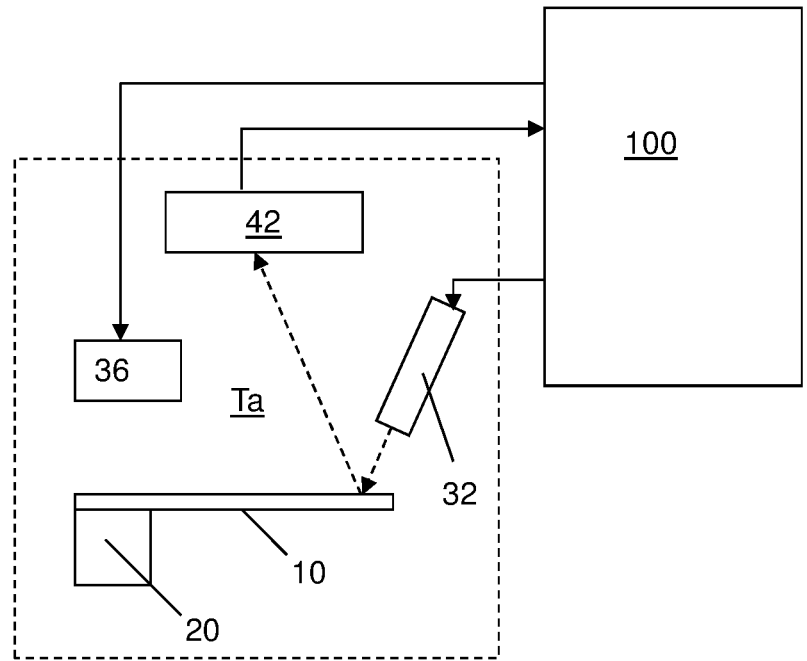
FIG. 2 shows a second embodiment of an arrangement according to the first aspect of the invention, FIG. 3 schematically shows a cantilever to be calibrated with the arrangements shown in FIG. 1 and FIG. 1A.

FIG. 1 shows an arrangement for calibrating a cantilever, such as a scanning probe microscope cantilever 10 (SPM cantilever). The cantilever 10, shown in more detail in FIG. 3, comprises at least a first and a second layer 14, 16 that have a mutually different thermal expansion coefficient. The arrangement further comprises an anchoring facility 20 for anchoring the cantilever 10 at a first end 12. The arrangement also comprises a temperature control facility for controllably causing a temperature distribution along the cantilever 10. In the embodiment shown the temperature control facility comprises a photon radiation source, such as a laser 32 and a control facility 134 for controlling a power level of the photon radiation source 32, for example a laser controller implemented as dedicated circuitry, a suitably programmed general purpose computer 100 or a combination thereof. Alternatively, or in addition an ambient temperature Ta may be controlled by a heating and/or a cooling element 36 as is illustrated in FIG. 2. In again another embodiment a controlled heating or cooling element 36 may be thermally coupled to the anchoring facility 20. A controller for controlling the controlled heating or cooling element 36 may be implemented as dedicated circuitry, a suitably programmed general purpose computer 100 or a combination thereof.

The arrangement further comprises a measuring facility for measuring a resulting spatial state of the cantilever, such as an amount of deflection of the cantilever. In the embodiment shown the measurement facility comprises a first facility formed by a photo-detector 42, that detects photon radiation (indicated by dashed lines) generated by the photon radiation source. The location where the reflected photon radiation hits the photo-detector 42 depends on the amount of deflection of the cantilever 10. The measurement facility further includes a processing facility 144 that computes the amount of deflection from the detected location.

Also other measuring facilities for measuring the deflection are available, such as optical interferometry facilities, capacitive sensing facilities. Also piezoresistive cantilevers are known. These cantilevers are fabricated with piezoresistive elements that act as a strain gauge. Using a Wheatstone bridge, strain in the cantilever due to deflection can be measured, but this method is not as sensitive as laser deflection or interferometry. Alternatively a deflection may be measured by an integrated nanophotonics sensor. Examples of integrated nanophotonics sensors are waveguide-based, monolithically integrated resonant interferometers, such as a Bragg-grating-based Fabry-Perot resonators, microspheres, microdisks, microtoroids, photonic crystal cavities and ring resonators. The processing facility 144 may be provided as dedicated circuitry, as a suitably programmed general purpose computer 100 or as a combination thereof. The arrangement further comprises a computation facility 150 for computing a mechanical property from the detected spatial state caused by controllably changing the temperature. The computation facility 150 may be provided as dedicated circuitry, as a suitably programmed general purpose computer 100 or as a combination thereof.

In the embodiment shown, the arrangement further includes a second facility 90, 145 for measuring a resonance frequency of the cantilever 10. In this embodiment the computation facility 150 also uses the measured resonance frequency in addition to the measured deflection or radius of curvature to compute the mechanical property. In the embodiment shown in FIG. 1, the second facility comprises an excitation element 90 arranged for causing a resonation of the cantilever and an analyzer 145 coupled to an output of the first facility, processing facility 144 to determine a frequency with which the cantilever 10 resonates. The analyzer 145 provides the determined frequency to the computation facility 150.

As mentioned above, it is important to accurately know the spring constant k of a cantilever in order to determine the force exerted on the tip of the cantilever from the deflection of the cantilever. The spring constant k [N/m] can be calculated as follows.

$$k = \frac{3E \cdot I}{L^3}, \text{ therein} \qquad (1)$$

E is the equivalent Youngs modulus of the cantilever beam [Pa]
I is the moment of inertia of the cantilever beam [m$^4$]
The product EI is also denoted as the bending stiffness [Nm$^2$].
L is the length of the cantilever [m].

Figure 3:
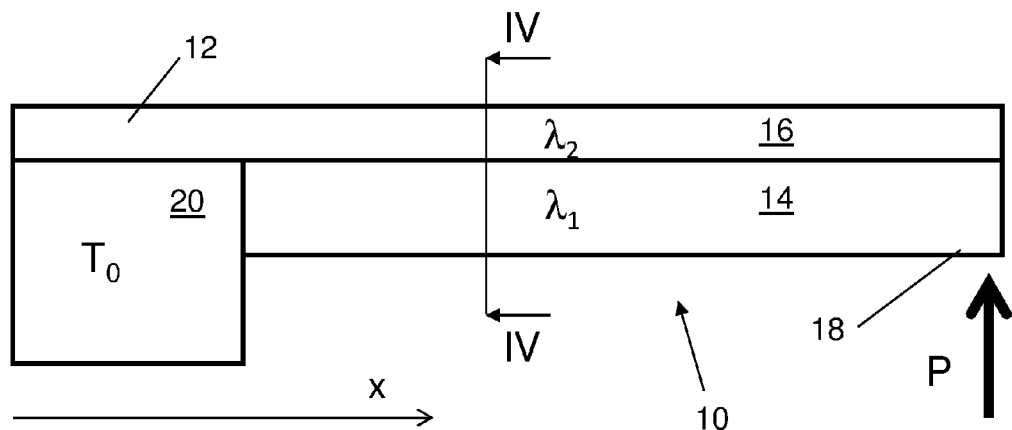
Figure 4:
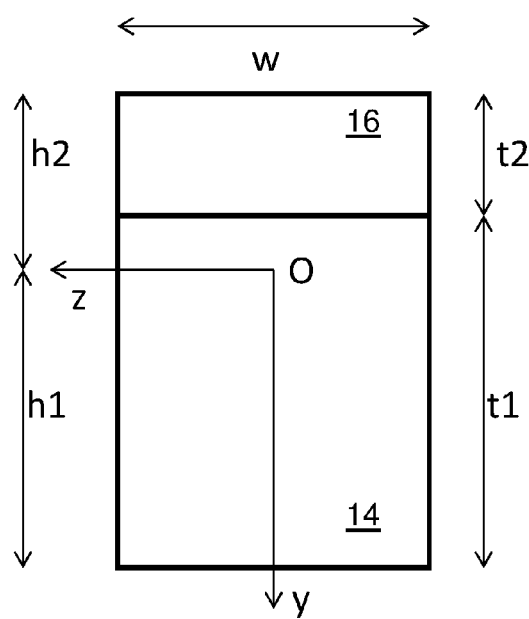
FIG. 4 shows a cross-section according to IV-IV in FIG. 3, FIG. 5 schematically shows a curvature of the cantilever to be calibrated as a function of ambient temperature.

However, in practice both the thickness and the Youngs modulus of the individual layers vary from batch to batch. As mentioned above, a cantilever as used for SPM purposes typically is provided in the form of a double layered beam 10 as shown in FIG. 3 and FIG. 4. Therein FIG. 4 shows a cross-section according to IV-IV in FIG. 3. The highly reflective cover layer 16 is typically substantially thinner than the substrate layer 14. By way of illustrative, but non-limiting example, the substrate layer 14 may have a thickness $t_1$ of 60 gm, and the cover layer 16 may have thickness $t_2$ of 60 nm. The moment of inertia I [m$^4$] of such a double layered beam is defined as follows:

$$I = \frac{1}{3}w \cdot h_1^3 + \frac{1}{3}w \cdot h_2^3 \qquad (2)$$

where:

$$h_1 = \frac{\frac{1}{2}E_1 w \cdot t_1^2 + E_2\left(t_1 + \frac{1}{2}t_2\right)w \cdot t_2}{E_1 w \cdot t_1 + E_2 w \cdot t_2} \qquad (3a)$$

$$h_2 = t_1 + t_2 - h_1 \qquad (3b)$$

Therewith the equivalent bending stiffness EI [N·m$^2$] of such a double layer beam defined as:

$$EI = \frac{w \cdot t_2^3 t_1 E_2 E_1}{12(t_1 E_1 + t_2 E_2)} K_1, \text{ wherein} \qquad (4)$$

$$K_1 = 4 + 6\frac{t_1}{t_2} + 4\left(\frac{t_1}{t_2}\right)^2 + \frac{E_1}{E_2}\left(\frac{t_1}{t_2}\right)^3 + \frac{E_2}{E_1}\frac{t_2}{t_1} \qquad (4a)$$

If by way of example, the following data is known:
t1=0.6 μm, t2=60 nm, E1=310 GPa, E2=79 GPa and w=40 μm, L=200 μm, it can be computed that the spring constant k of the assembly equals 0.091 N/m.

In an embodiment of a method according to the present invention an estimation of the thickness t1, t2 of the layers 14, 16 is obtained from the thermomechanical behaviour of the cantilever 10 by controllably causing a temperature distribution along the cantilever and measuring a resulting spatial state of the cantilever. In an embodiment controllably causing a temperature distribution T(x) along the cantilever is realized by irradiating a free end 18 of the cantilever 10 with a photon radiation having a known power P[W].

Therewith a temperature distribution T(x) in the longitudinal direction of the cantilever 10 is obtained complying with the following relation:

$$T(x) - T_0 = \left(\frac{x}{L}\right) \cdot \frac{P}{G} \qquad (5)$$

Therein L[m] is the distance between the clamped end 12 and the free end 18 and G [W/K] is the equivalent conductance, which can be determined as follows.

$$G = G_1 + G_2, \text{ with} \qquad (6)$$

$$G_1 = \lambda_1 \cdot \frac{A_1}{L}, \text{ and} \qquad (6a)$$

$$G_2 = \lambda_2 \cdot \frac{A_2}{L} \qquad (6b)$$

Therein $G_1$, $G_2$ [W/K] are the conductances of the layers 1,2 respectively, and $\lambda_1, \lambda_2$ [W/mK] are the specific conductances of the materials used for the first and the second layer 14, 16 respectively.

In an exemplary embodiment SiN and Au are used for the first and the second layer 14, 16 respectively, having respective specific conductances of $\lambda_{SiN}$=30 W/mK and $\lambda_{Au}$=318 W/mK. Furthermore in said exemplary embodiment the layers 14, 16 of the cantilever have the following dimensions, w=40 μm, L=200 μm, $t_1$=0.6 μm, $t_{2=60}$ nm. In that embodiment the equivalent conductance G equals 8.4*10$^{-6}$ W/K. It is noted that the thickness $t_1$, $t_2$ of the layers 14, 16 of the cantilever can be determined indirectly, Provided that the total thickness t and the equivalent heat conductance G of the cantilever 10 is known, the thickness $t_1$ and $t_2$ of the layers 14, 16 can be determined from the following two equations 7a and 7b below:

$$t = t_1 + t_2 \qquad (7a)$$

$$G = k_1 \frac{wt_1}{L} + k_2 \frac{wt_2}{L} \qquad (7b)$$

Annex 1 describes another approach to determine the thickness $t_1$, $t_2$ of the individual layers in case the total thickness t is unknown.

The equivalent conductance G can be determined from the temperature difference between the ends 12, 18 of the cantilever caused by the applied power, according to $$G = \frac{P}{\Delta T} \qquad (8)$$

Due to the fact that the layers 14, 16 have a mutually different thermal expansion coefficient, $\alpha_1$ and $\alpha_2$, and that a controlled temperature distribution T(x) within the cantilever is caused by heating the cantilever, the cantilever will deform. The amount of deformation indicated by radius of curvature $\kappa$[m$^{-1}$] is proportional to the temperature gradient according to the following linear relationship. Therein $T_0$ is the stress free temperature, i.e. the temperature wherein no stresses occur due to different thermal expansion coefficients of the layers of the cantilever 10. Furthermore, $T_1$ is the ambient temperature, which is presumed to be the temperature at the clamped end 12, and $T_2$ is the temperature at the free end 18 of the cantilever.

$$\kappa = \beta \cdot [T(x) - T_0] \qquad (9)$$

The temperature distribution T(x) is substantially linear in x, so that $$T(x) = (T_2 - T_1)\frac{x}{L} + T_1 \quad (10)$$

The proportionality factor $\beta[m^{-1}K^{-1}]$ therein is computed as follows:

$$\beta = \frac{6\Delta\alpha}{t_2} h \cdot m \left[ \frac{1+h}{1 + 2h \cdot m(2 + 3h + 2h^2 + h^4 m^2)} \right] \quad (11)$$

With $$h = \frac{t_1}{t_2}, \ m = \frac{M_1}{M_2}, \ M_{1,2} = \frac{E_{1,2}}{1 - v_{1,2}} \text{ and } \Delta\alpha = \alpha_1 - \alpha_2 \quad (12a, b, c, d)$$

Therein $v_{1,2}$ is the Poisson ratio of the cantilever.
Now the deflection $\delta(x)$ for position x can be obtained by two-fold integration of the curvature obtained with equation 11, i.e.

$$\delta(x) = \int_{u=0 \text{to} x} \int \kappa du^2 = \beta \left[ \frac{(T_2 - T_1)}{6L} x^3 + \frac{(T_1 - T_0)}{2} x^2 \right] \quad (13)$$

Figure 5:
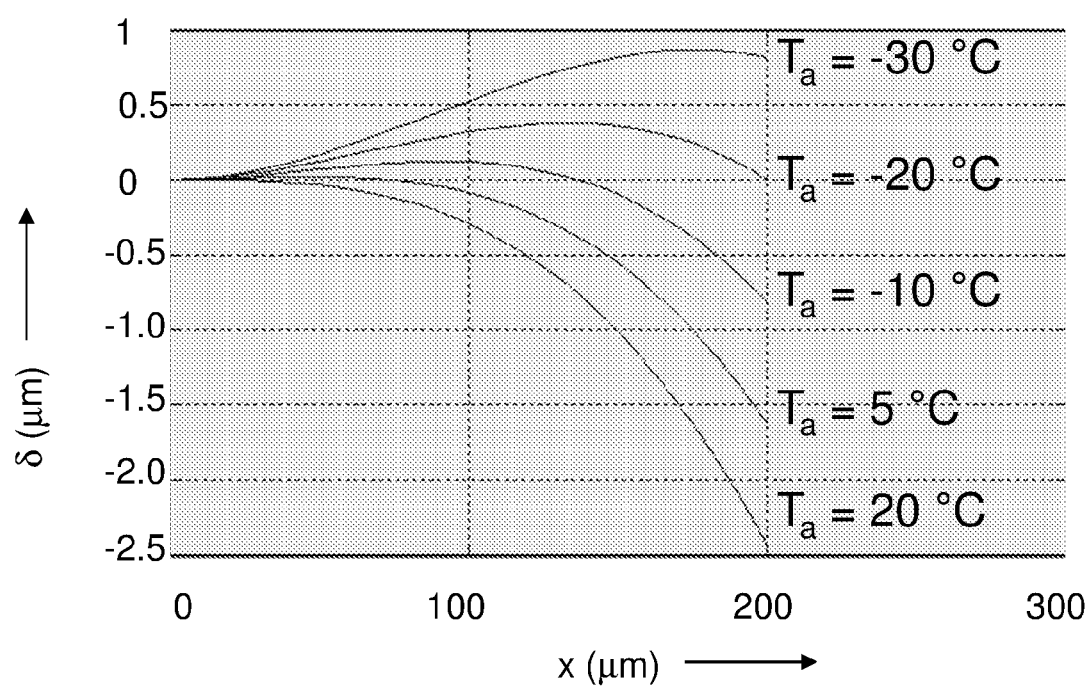

In another embodiment, a temperature distribution along the cantilever is controlled by controlling an ambient temperature. FIG. 5 shows a simulated deflection $\delta(x)$ of the cantilever as a function of the position in the longitudinal direction, i.e. the distance x from the position where the cantilever is clamped, for 5 different values of the ambient temperature Ta: −30, −20, −10, 5 and 20° C. The cantilever is heated by a radiation source having a power of 1 mW at its end 18 remote from the clamped end 12. For this simulation it was presumed that the first layer has a thickness of 0.6 μm and a Young modulus of 310*10⁹ Pa and that the second layer has a thickness of 60 nm and a Young modulus of 79*10⁹ Pa. Furthermore it is presumed that the length L and the width w of the cantilever 10 are 200 μm and 40 μm respectively.

Figure 6:
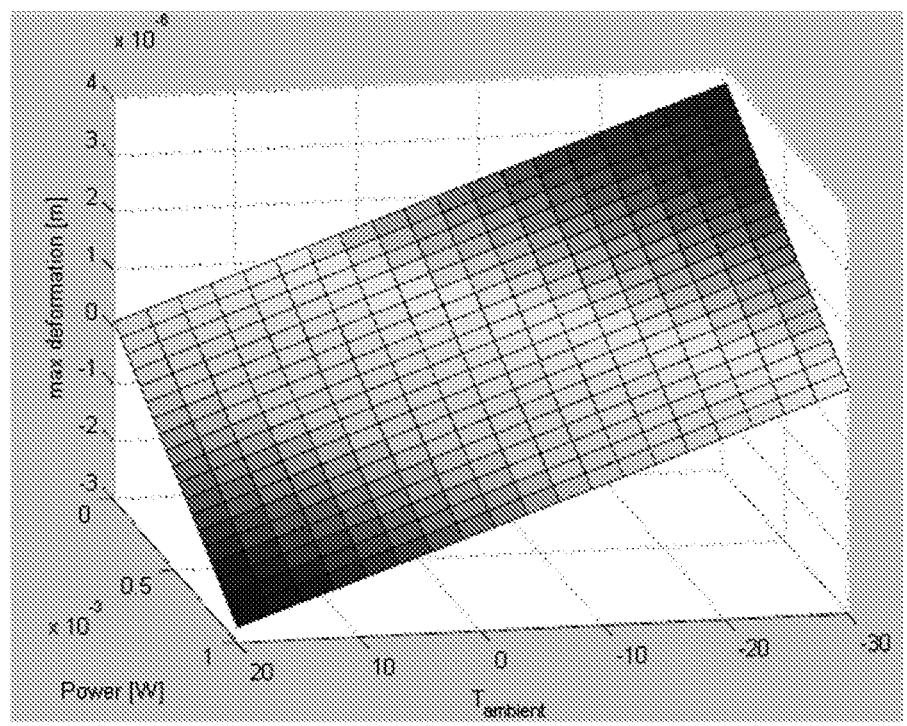
FIG. 6 illustrates the relation between applied heating power P, ambient temperature Ta and deflection δ of a cantilever.

FIG. 6 illustrates the relation between the applied laser power P, the ambient temperature Ta and the deflection δ at the free end (remote from the clamped end) of the cantilever. It was verified by finite element analysis that the following relations are substantially linear:
  The ambient temperature and the deflection δ.
  The temperature and the position along the cantilever.
  The maximum temperature and the applied power.

Figure 7:
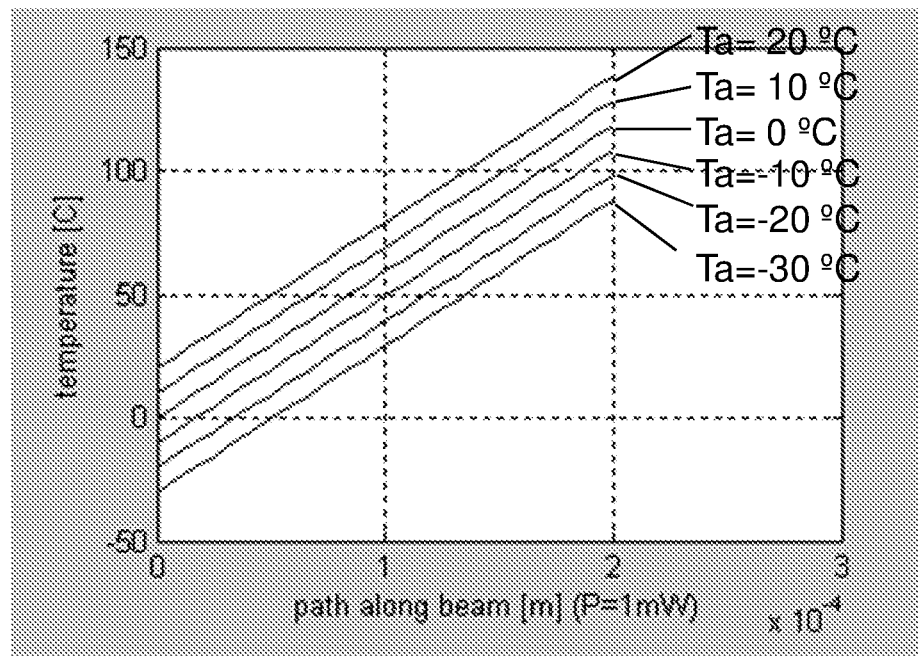
FIG. 7 shows a temperature distribution for different values of the ambient temperature.

FIG. 7 shows the temperature as a function of the position along the cantilever for 6 different values of the ambient temperature Ta. Therein the temperature at the clamped end 12 is equal to the ambient temperature.

Figure 8:
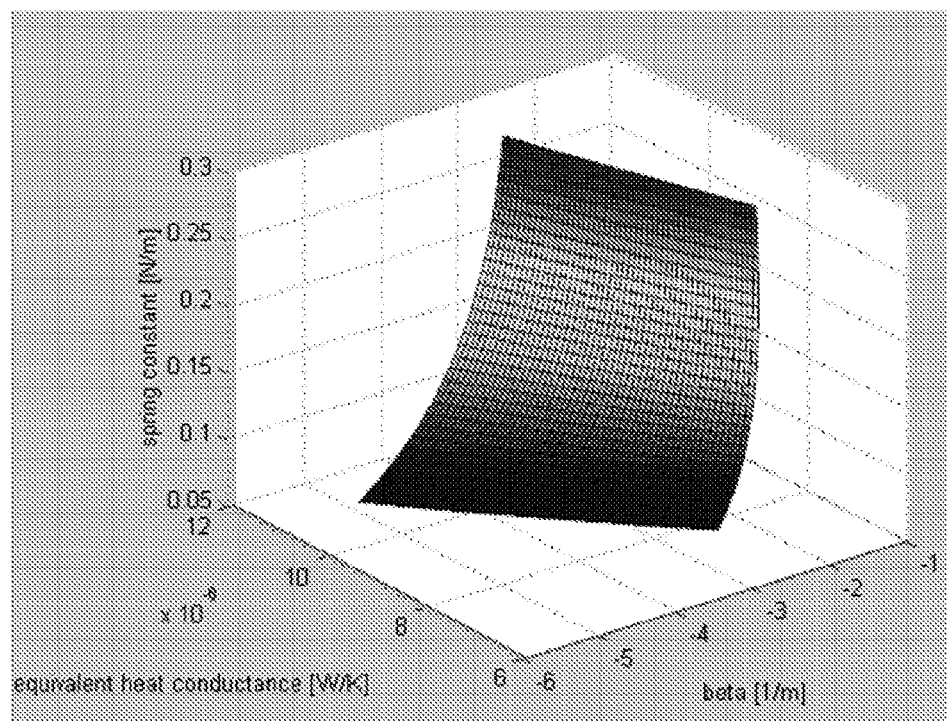
FIG. 8 illustrates the relation between spring constant, equivalent conductance and curvature at a predetermined location of the cantilever for a predetermined value of the applied heating power P, and the ambient temperature Ta.

In an embodiment, the spring constant k is calculated from the curvature κ and the heat conductance G of the cantilever. FIG. 8 shows how the spring constant k of the cantilever, the equivalent conductance G and the curvature κ, indicated by its reciprocal value β in FIG. 8, are mutually related. The relationship was determined according to a finite element simulation presuming controlled circumstances for the ambient temperature Ta and the power P with which the cantilever is irradiated. In this simulation it was presumed that the first layer 14 of the cantilever 10 has a thickness of 0.6 μm and a Young modulus of 310 GPa and that the second layer 16 of the cantilever 10 has a thickness of 60 nm and a Young modulus of 79 GPa. In practice the layers may be non-homogeneous, e.g. the thickness of the first layer may vary, e.g. between 0.3 and 0.9 μm. Also the thickness of the second layer may vary, e.g. between 30 and 90 nm. Furthermore it is presumed that the length L and the width w of the cantilever 10 are 200 μm and 40 μm respectively. In this simulation it is further presumed that the cantilever is heated by a radiation source having a power of 1 mW at its end 18 remote from the clamped end 12 and that the ambient temperature Ta is 20° C.

Accordingly, after the curvature κ and the heat conductance G of the cantilever are determined experimentally under the same controlled circumstances, the spring constant k can be determined from these values using the relationship obtained by simulation.

This embodiment of the method is very suitable if the Young modulus of the layers is known with sufficient accuracy. In some situations however, this may not be the case. For example, in some cases the Young modulus is known only with an accuracy of about 10%.

Figure 9:
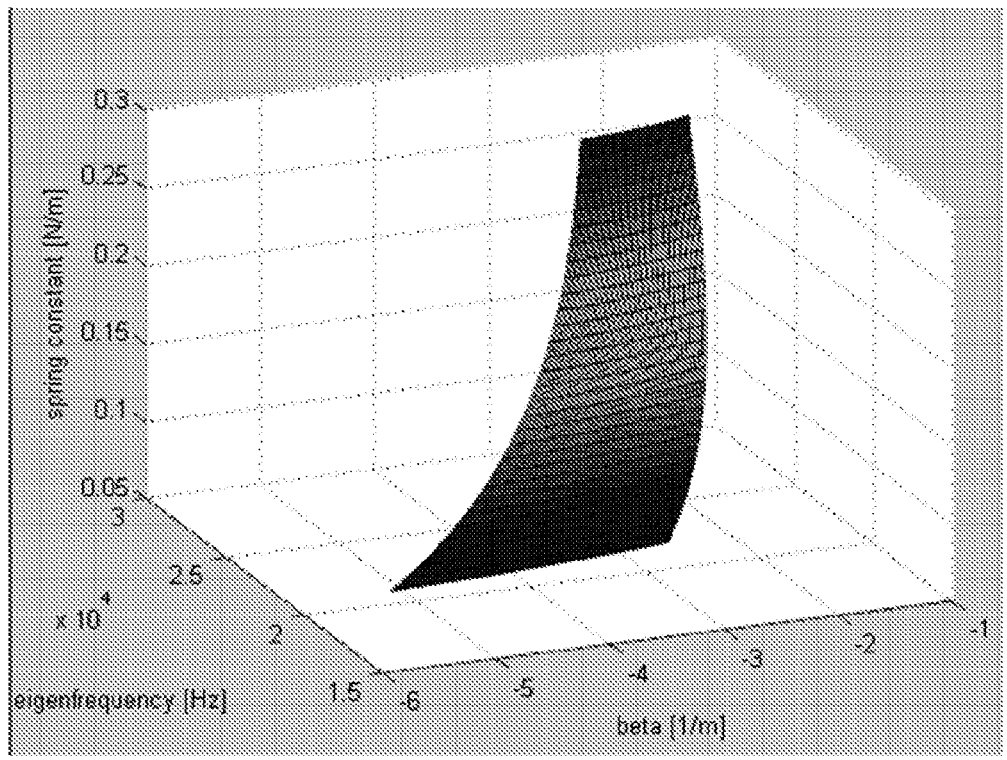
FIG. 9 illustrates the relation between spring constant, frequency and curvature at a predetermined location of the cantilever for a predetermined value of the applied heating power P, and the ambient temperature Ta.

A further embodiment is provided that does not require prior knowledge of the Young modulus of the layers. According to this method, the spring constant k of the cantilever 10 is determined from the curvature κ and the eigenfrequency f of the cantilever. FIG. 9 shows a relationship between these variables that was obtained using a finite element method. Therein the curvature κ is indicated by its reciprocal value β. In this simulation the same values for the dimensions of the cantilever 10 and its layers 14, 16 were used as for the simulation described with reference to FIG. 8. Also the values presumed for the Young modulus of the individual layers 14, 16, the power P of the laser and the ambient temperature Ta are the same. Accordingly, in this method the curvature κ and the eigenfrequency f of the cantilever are experimentally determined under the same controlled circumstances as were used to obtain the relationship, and subsequently, the spring constant k of the cantilever is determined from these values using the relationship obtained by simulation.

According to a still further embodiment of the method according to the present invention, the stiffness is calculated from a first and a second eigenfrequency of the cantilever for two different temperatures. Due to the thermal expansion of the cantilever 10, independent measurements are obtained from which a mechanical property of the cantilever can be obtained. In practical cases it may often be assumed that the mechanical properties of the cantilever can be approximated by the mechanical properties of one of its layers. For example, typically a SiN layer is used as the first layer 14, having a thickness that is 10 times higher than that of the second layer 16, and that has a Young modulus that is 3 times higher than the Young modulus of the second layer.

The eigenfrequencies $f_n$ of the cantilever 10 depend on its length L, mass m and its equivalent stiffness EI, according to the following relation:

$$EI \frac{\partial^4 u(x,t)}{\partial x^4} + C \frac{\partial u(x,t)}{\partial t} + (\rho A) \frac{\partial^2 u(x,t)}{\partial t^2} = P(x,t) \quad (14)$$

Where:
u is the deflection of the cantilever
x is the coordinate along the length of the cantilever
t is time,
C is the damping factor, ρ is the density of the cantilever A is the cross section of the cantilever and P is the thermal load.

Solving the above differential equation the eigenfrequency f follows:

$$f_n = \frac{\gamma_n^2}{2\pi}\sqrt{\frac{EI}{mL^3}} \quad (15)$$

Therein $\gamma_n$ is a dimensionless constant. The values thereof for the first 3 eigenfrequencies are: $\gamma_1=1.8751$, $\gamma_2=4.6941$, $\gamma_3=7.8548$ By controllably changing the temperature distribution, e.g. from a first uniform distribution with a first temperature T1, to a second uniform distribution with a second temperature $T_2$, the length L of the cantilever can be varied. The temperature distribution can be controlled for example by controlling the ambient temperature or by controllably irradiating the cantilever with a laser. The variation in length L is substantially proportional to the variation in temperature according to the following relation.

$$L_1 = L(1+\alpha \cdot \Delta T) \quad (16)$$

The corresponding shift $\Delta f_n$ in eigenfrequency $f_n$ is $$f_n = \frac{\gamma_n^2}{2\pi}\sqrt{\frac{EI}{m}}\left(\sqrt{\frac{1}{L^3}} - \sqrt{\frac{1}{L_1^3}}\right) \quad (17)$$

By measuring for both temperatures one of the eigenfrequencies and the length of the cantilever, the equivalent stiffness of the cantilever can be determined.

In another embodiment, the density $\rho[kg/m^3]$ of a cantilever is determined from a transient experiment. Therein a transient heat load is applied to the cantilever and the transience to an equilibrium state is monitored. The temperature distribution T(x,t) of the cantilever is described by the following differential equation.

$$\frac{\partial T}{\partial t} = \psi\left(\frac{\partial^2 T}{\partial x^2}\right), \text{ with } \psi = \frac{\lambda}{c_p \rho} \quad (18)$$

Therein $c_p$ is the equivalent heat capacity, which is assumed to be known, and $\lambda$ is the equivalent heat conductance coefficient. The value of $\lambda$ can be determined from the value of the equivalent heat conductance. The equivalent heat conductance G can be determined from the temperature difference between the ends 12, 18 of the cantilever caused by the applied power, according to $$G = \frac{P}{\Delta T} \quad (19)$$

The equivalent thermal diffusivity $\psi$ will be measured. Thus, the equivalent density ρ can be calculated.

This one-dimensional heat equation can be solved using the following initial and boundary conditions:

$$T(x, t=0) = (t_2 - T_1)\frac{x}{L} + T_1, \quad (19a)$$

$$T(x=0, t) = T_1, \text{ and} \quad (19b)$$

$$T(x=L, t=\infty) = T_1 \quad (19c)$$

Figure 10:
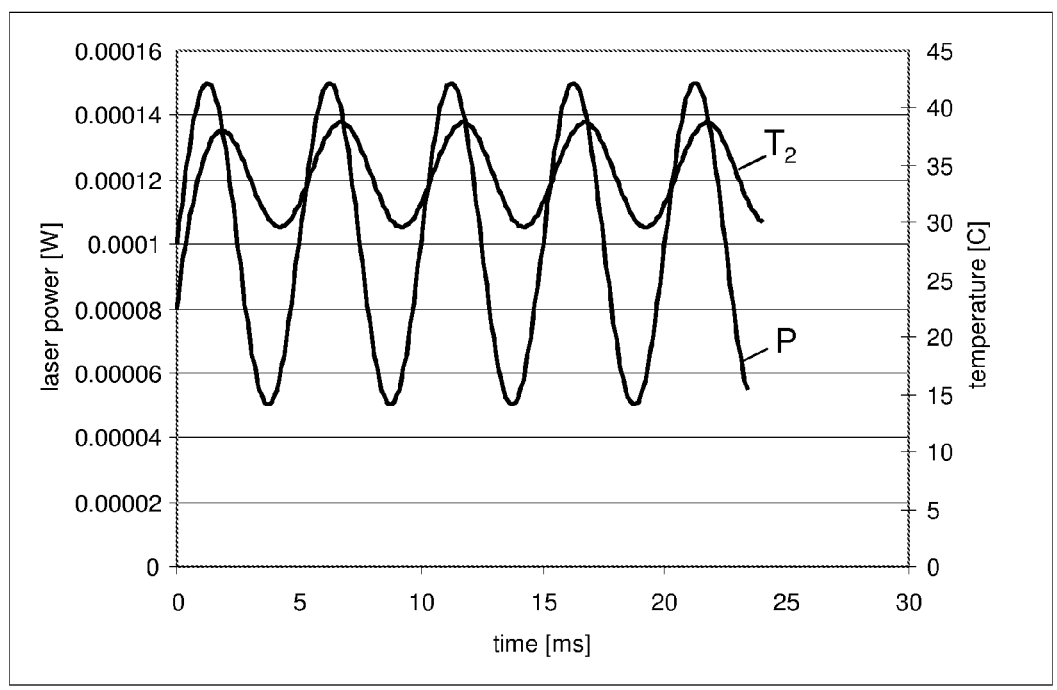
FIG. 10 shows an example of an applied transient heat load to a cantilever beam, as well as the resulting temperature at the tip of the cantilever beam.

An example of a transient experiment is given in FIG. 10. FIG. 10 shows the applied laser power P and the temperature $T_2$ at the free end 18 of the cantilever 10 as a function of time. The scale on the left side of the figure indicates the applied laser power in W. The scale on the right side of the figure indicates the temperature in ° C. The laser power was sinusoidally varied between about 0.05 mW and 0.15 mW with a period of 5 ms.

As indicated above, the equivalent heat conductance G can be determined from the temperature difference between the ends 12, 18 of the cantilever caused by the applied power, according to equation 19 above. Therein, the temperature difference ΔT is the difference between the temperature at the position where the cantilever is heated, typically at its free end 18, and the base temperature. The base temperature can be measured by various known methods, e.g. using a thermocouple, the temperature at the free end may be measured by a pyrometer for example. Alternatively, a measurement of the temperature at the position where the cantilever is heated can be obviated by a procedure as described below. In this procedure the equivalent heat conductance G is determined from a combination of measurements, described in detail in Appl. Phys. Lett. 92, 063509 (2008). This method can be summarized as follows In a first measurement a free end portion of the cantilever is heated, and a deflection is measured for at least two mutually different values of the applied heating power. In a second measurement the resulting deflection is measured for at least two mutually different values of the base temperature. The measurements each result in a sensitivity factor. The equivalent conductance G is determined from the ratio of these sensitivity factors. The sensitivity factor $S_P$ for the absorbed power P is:

$$S_p = \frac{\partial w}{\partial P} = \frac{HL^2}{3G} \quad (20a)$$

Therein, w is the deflection of the cantilever at the free end, L is the length of the cantilever and H is a constant dependent on the properties and the thickness of the materials used for the cantilever.

To determine the sensitivity factor $S_P$, it is sufficient that the deflection w is measured for at least two mutually different values of the applied heating power P. In that case the sensitivity factor is determined as the difference of the measured deflections divided by the difference of the measured values for the heating power. Alternatively however, the deflection w may be measured for a larger number of values of the applied heating power P, and the sensitivity factor $S_P$ may be determined as the slope of a line that best approximates, e.g. according to a least squares fit, the measured value of the deflection as a function of the absorbed heating power P.

The sensitivity factor ST for the base temperature $T_0$ is:

$$S_T = \frac{\partial w}{\partial T_0} = 3HL^2 \qquad (20b)$$

To determine the sensitivity factor ST, it is sufficient that the deflection w is measured for at least two mutually different values of the base temperature $T_0$. In that case the sensitivity factor is determined as the difference of the measured deflections divided by the difference of the values for the base temperature. Alternatively however, the deflection w may be measured for a larger number of values of the base temperature $T_0$, and the sensitivity factor ST may be determined as the slope of a line that best approximates, e.g. according to a least squares fit, the measured value of the deflection as a function of the base temperature $T_0$.

Subsequently, the equivalent conductance G can be determined as:

$$G = \frac{1}{9}\frac{S_T}{S_P} \qquad (21)$$

In the embodiment described here, the deflection of the cantilever is determined from the position where a laser beam reflected on the surface of the cantilever hits a photodetector. It is noted that the same procedure could be applied with other methods for determining the deflection, as any proportionality factor disappears by the division of the two sensitivity factors.

A still other method based on measuring a phase lag between a power of a periodically varying heat flow applied to the cantilever and a rotation of the cantilever caused by said applied heat flow is described below. The following general form of the heat equation is used therein.

$$\frac{\partial T(x,t)}{\partial t} = \psi \frac{\partial^2 T(x,t)}{\partial x^2} - B*(T(x,t) - T_{env}) + f(x,t) \qquad (22)$$

Therein B is the effective convective heat transfer coefficient in [1/s], f is a source function and $\psi$ is the thermal diffusivity as specified in equation 18 before.

Presuming that the base temperature is constant and equal to the environmental temperature $T_{env}$, and further defining:

$$\hat{T}(x,t) = T(x,t) - T_{env}$$

Equation 22 reduces to $$\hat{T}_t = \psi \hat{T}_{xx} - B\hat{T} + f(x,t) \qquad (23)$$

Therein the subscripts indicate the partial derivatives with respect to t and x. Now the following assumptions are made:
1. The cantilever beam is arranged in an evacuated space, therewith eliminating the convection term as B=0.
2. The following boundary conditions (24a,b,c) apply:

$$\hat{T}(0,t) = T_1$$

$$\hat{T}_x(L,t) = \frac{P_{max} + P_{min}}{2} + \frac{P_{max} + P_{min}}{2}\sin(\omega t)$$

$$\hat{T}(x,0) = T_1$$

Figure 11:
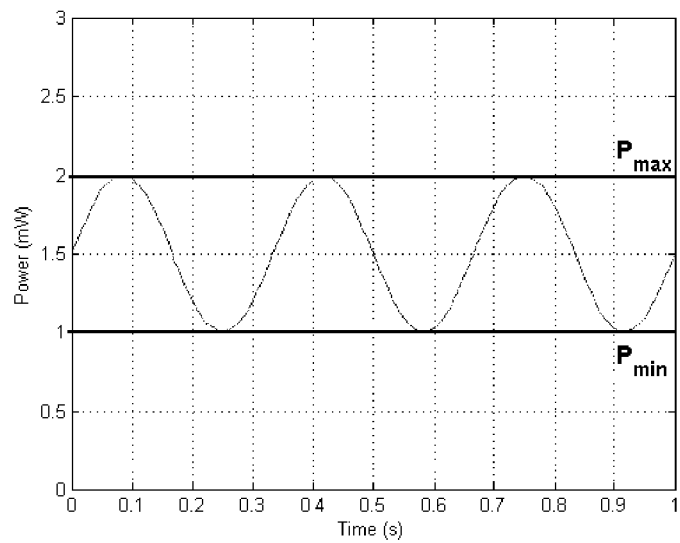
FIG. 11 illustrates a periodically varying heat load applied to a free end of a cantilever.

The second one of the boundary conditions replaces the source term. This second boundary condition represents a power source (e.g. a laser beam) that heats the cantilever beam with a power that periodically varies between a minimum value $P_{min}$ and a maximum value $P_{max}$ with a frequency $\omega$ at a position x=L, as is shown in FIG. 11.

Furthermore, $T_1$ is the base temperature. It can be shown that the tangent tan $\phi$ of the phase lag between the input power and the temperature of the tip is:

$$\tan\phi = \frac{\sum_{n=1}^{\infty}\frac{-\omega}{\psi^2\lambda_n^4 + \omega^2}}{\sum_{n=1}^{\infty}\frac{-\psi\lambda_n^2}{\psi^2\lambda_n^4 + \omega^2}} \qquad (25)$$

Basically the temperature and can be measured, e.g. with a pyrometer and consequently the value of the phase lag measured as a function of the frequency $\omega$. However, as a more practical approach, the phase lag of the rotation of the cantilever tip is measured.

It can be shown that this rotational phase lag is related as follows to the frequency $\omega$.

$$\tan\phi = \frac{\sum_{n=1}^{\infty}(-1)^{n+1}\frac{\omega}{\lambda_n(\psi^2\lambda_n^4 + \omega^2)}}{\sum_{n=1}^{\infty}(-1)^{n+1}\frac{\psi\lambda_n^2}{\lambda_n(\psi^2\lambda_n^4 + \omega^2)}} \qquad (26)$$

Figure 12:
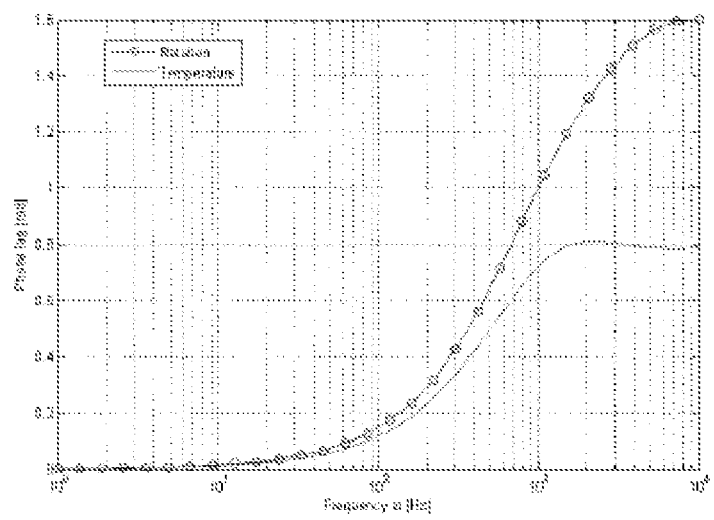
FIG. 12 illustrates (1) a phase lag between the temperature of the free end and the applied power of the heat load, and (2) a phase lag between the rotation of the free end and the applied power of the heat load, FIG. 13 schematically shows an embodiment of a scanning probe microscope according to the second aspect of the invention.

This relation 26 and the relation 25 for the temperature phase lag are shown in FIG. 12.

In case the convection cannot be eliminated the phase lag can be calculated by a numerical approximation.

Figure 13:
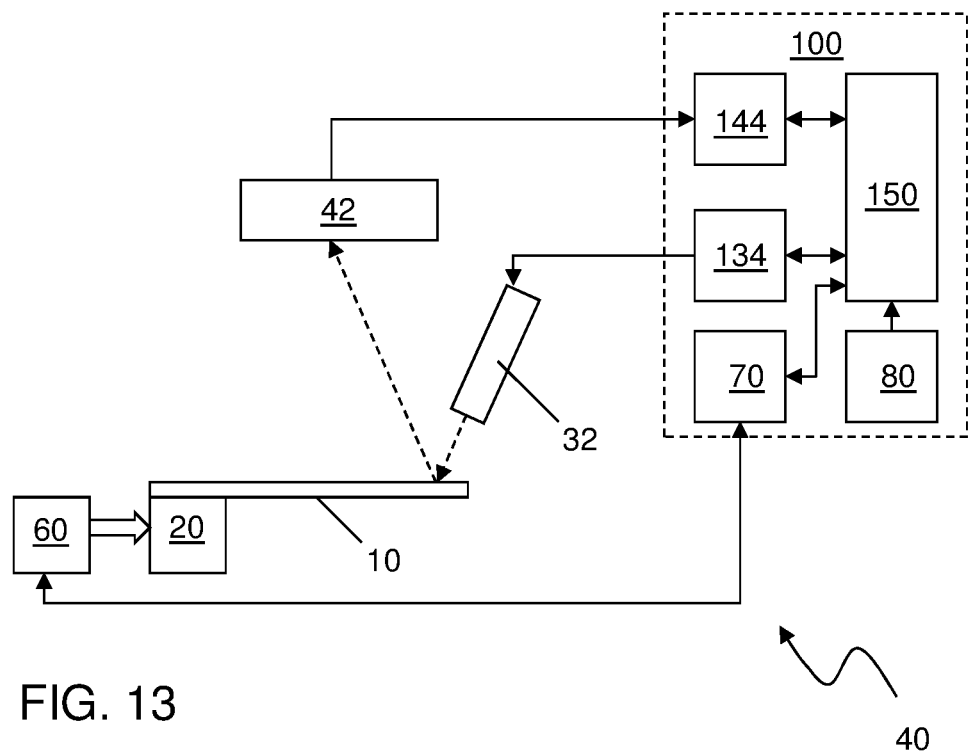

FIG. 13 shows a scanning probe microscope 40 that includes an arrangement for calibrating a cantilever according to the present invention, for example an arrangement as described with reference to FIG. 1 or FIG. 2. The microscope further includes an actuator facility 60 for controllably positioning the anchoring facility 20. The actuator facility is controlled by a control facility 70. The control facility 70 may be provided as dedicated circuitry, as shown in FIG. 11 as a suitably programmed general purpose computer 100 or as a combination thereof. The scanning probe microscope 40 has a mode control facility 80 that selects an operational mode from at least one of a calibration mode and a normal operation mode. In the calibration mode the scanning probe microscope 40 performs one or more of the calibration methods as described with reference to FIGS. 3 to 10 above to determine a mechanical property of the cantilever 10. In the normal operation mode the scanning probe microscope 40 can be used for measurements.

Figure 14:
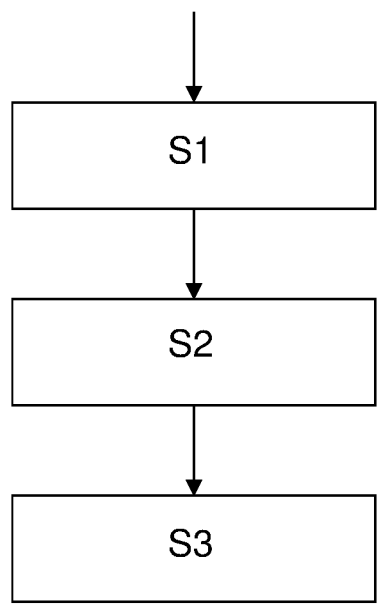
FIG. 14 schematically shows an embodiment of method according to the third aspect of the invention.

FIG. 14 schematically shows a method for calibrating a cantilever, such as a scanning probe microscope cantilever 10 (SPM cantilever). The cantilever to be calibrated comprises at least a first and a second layer 14, 16 having a mutually different thermal expansion coefficient. In a first step S1 of the method a temperature distribution along the cantilever is controllably caused, such as a linear temperature distribution, wherein the temperature linearly changes from a relatively high temperature at a first end, and a relatively low temperature at a second end. Therewith the cantilever may be clamped at a first end that maintains the cantilever 10 at a reference temperature. In a second step S2 a spatial state is measured that is assumed by the cantilever when it has assumed the controllably caused temperature. The spatial state is for example a radius of curvature as a function of the distance along the cantilever. In addition the measured spatial state may be a resonance frequency of the cantilever measured.

In a third step S3 the spring constant of the cantilever beam is computed from the observed spatial state caused by controllably applied temperature distribution. The spring constant is determined for example from the measured radius of curvature or the deflection of the cantilever preferably in combination with the measured resonance frequency.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). Control functions may be carried out by dedicated hardware (ASICs), by a suitably programmed general purpose processor or by a combination thereof. Various control functions may be realized by a common component.

Annex 1: Thickness determination
The 1-dimensional heat equation can be written as:

$$kAu_{xx} = c_p \rho A u_t$$

In which $\lambda$ is the equivalent thermal conductivity, A is the cross sectional area, and $c_p$ is the specific heat capacity, and $\rho$ is the density.

The thermal conductance of a double layered cantilever can be written as:

$$\lambda A = (k_1 t_1 + k_2 t_2) w$$

Therein w represents the width of the beam,
$k_{1,2}$ are the thermal conductivity values of the involved materials.
The heat capacity can also be written as:

$$c_p \rho A = (c_{p,1} \rho_1 t_1 + c_{p,2} \rho_2 t_2) w$$

With the thermal diffusivity $\psi$ defined as:

$$\psi = \frac{k}{\rho c_p}$$

This results in the final expression for the thermal diffusivity:

$$\psi = \frac{k_1 t_1 + k_2 t_2}{c_{p,1} \rho_1 t_1 + c_{p,2} \rho_2 t_2} \tag{A1.1}$$

According to equation 7b introduced earlier, the effective conductance can be expressed as:

$$G = (k_1 t_1 + k_2 t_2) \frac{w}{L} \tag{A1.2}$$

Combining these equations A1.1 and A1.2 the following equations are obtained for computing the thicknesses $t_1$ and $t_2$.

$$t_2 = \frac{GL\left(\frac{1}{D} - \frac{\rho_1 c_{p,1}}{k_1}\right)}{w\left(\rho_2 c_{p,2} - \frac{\rho_1 c_{p,1} k_2}{k_1}\right)} \tag{A1.3}$$

And $$t_1 = \frac{GL}{wk_1} - \frac{k_2}{k_1} t_2 \tag{A1.4}$$

What is claimed is:

1. An arrangement for calibrating a cantilever, the cantilever comprising at least a first and a second layer having mutually different thermal expansion coefficients, the arrangement comprising:
   a temperature control facility configured to controllably cause a temperature distribution along the cantilever,
   a measuring facility configured to measure a resulting spatial state of the cantilever, and
   a computation facility configured to compute a mechanical property from the resulting spatial state corresponding to said caused temperature distribution,
   wherein said measuring facility comprises a first facility configured to measure a deflection or a radius of curvature of the cantilever, and a second facility configured to measure a resonance frequency of the cantilever, and wherein the computation facility is configured to use the measured resonance frequency as well as the measured deflection or radius of curvature to compute the mechanical property.

2. An arrangement according to claim 1, wherein said measuring facility includes a first facility is an optical sensor configured to sense a beam reflected by the radiation source.

3. An arrangement according to claim 1, wherein the first facility is an optical sensor configured to sense a beam reflected by the radiation source, and wherein the second facility comprises an excitation element configured to cause resonation of the cantilever and an analyzer coupled to an output of the first facility configured to determine a frequency with which the cantilever resonates.

4. A scanning probe microscope comprising an arrangement according to claim 1, the microscope further comprising an anchoring facility configured to anchor the cantilever at a first end, an actuator facility configured to controllably position the anchoring facility, the computation facility configured to operate in a mode selected from at least the group consisting of a first, calibration mode, and a second, normal operational mode.

5. A method for calibrating a cantilever, the cantilever comprising at least a first and a second layer having mutually different thermal expansion coefficients, the method comprising the steps of:
   controllably causing a temperature distribution along the cantilever,
   measuring a spatial state of the cantilever,
   measuring a resonance frequency of the cantilever, and computing a mechanical property from the measured resonance frequency as well as a measured deflection or radius of curvature caused by controllably changing the temperature.

6. The method according to claim 5, wherein the step of controllably causing a temperature distribution is performed by controllably heating the cantilever with a photon radiation source.

7. The method according to claim 5, wherein the step of controllably causing a temperature distribution is performed by changing an ambient temperature.

8. The method according to claim, comprising the steps of:
determining in a simulation, for a predetermined amount of heat power (P) supplied to the cantilever and for a predetermined ambient temperature (Ta) value, a first empirical relation between the curvature ($\kappa$) or deflection ($\delta$) of the cantilever, its equivalent conductance (G) and its spring constant, k
applying said predetermined amount of heat power (P) to a cantilever to be calibrated while maintaining said ambient temperature (Ta) at the predetermined ambient temperature (Ta) value,
detecting a resulting curvature ($\kappa$) or deflection ($\delta$) of the cantilever, and
determining the spring constant (k), from said detected curvature ($\kappa$) or deflection ($\delta$) and the equivalent conductance (G) using the first empirical relation.

9. The method according to claim, comprising the steps of:
determining in a simulation, for a predetermined amount of heat power (P) supplied to the cantilever and for a predetermined ambient temperature (Ta) value, a second empirical relation between the a resonance frequency (f) of the cantilever, its equivalent conductance (G) and its spring constant (k),
applying said predetermined amount of heat power (P) to a cantilever to be calibrated while maintaining said ambient temperature (Ta) at the predetermined ambient temperature (Ta) value,
detecting a resulting resonance frequency (f) of the cantilever, and
determining the spring constant, from said detected resonance frequency (f) and the equivalent conductance (G) using the second empirical relation.

10. The method according to claim, comprising the steps of:
applying an initial temperature distribution to a cantilever to be calibrated,
allowing an equilibrium temperature distribution to settle,
measuring the temperature distribution along the cantilever as a function of time, and
calculating a density from the measured temperature distribution along the cantilever as a function of time.

11. The method according to claim, comprising determining an equivalent density $\rho$ from a measured thermal diffusivity of a cantilever beam.

* * * * *